United States Patent [19]

Barder et al.

[11] Patent Number: 4,977,243

[45] Date of Patent: Dec. 11, 1990

[54] SEPARATION OF STEROLS FROM LOW-ACID FEEDS WITH MAGNESIUM SILICATE AND METHYL-TERT-BUTYL ETHER DESORBENT

[75] Inventors: Timothy J. Barder, Addison; W. Brian Bedwell, Chicago; Steven P. Johnson, Prospect Heights, all of Ill.

[73] Assignee: UOP, Des Plaines, Ill.

[21] Appl. No.: 291,013

[22] Filed: Dec. 28, 1988

[51] Int. Cl.$^5$ .......................... C09F 1/02; B01D 15/00
[52] U.S. Cl. ................................... 530/208; 530/205; 210/674; 210/690
[58] Field of Search ................. 210/690, 674; 530/205, 530/208

[56] References Cited

U.S. PATENT DOCUMENTS

| | | | |
|---|---|---|---|
| 2,352,547 | 6/1944 | Jenkins | 260/97.5 |
| 2,354,812 | 8/1944 | Jenkins | 260/97.5 |
| 2,363,925 | 11/1944 | Adams | 260/97.5 |
| 2,985,589 | 5/1961 | Broughton | 210/34 |
| 3,040,777 | 6/1962 | Carson et al. | 137/625.15 |
| 3,422,848 | 1/1969 | Liebman et al. | 137/625.15 |
| 3,706,812 | 12/1972 | De Rosset et al. | 260/674 SA |
| 3,840,570 | 10/1974 | Julian | 260/397.25 |
| 4,642,397 | 2/1987 | Zinnen et al. | 568/934 |
| 4,664,807 | 5/1987 | Van Dam et al. | 210/635 |
| 4,747,937 | 5/1988 | Hilfman et al. | 210/690 |
| 4,761,222 | 8/1988 | Carter et al. | 208/322 |
| 4,849,112 | 7/1989 | Barder et al. | 210/690 |
| 4,882,065 | 11/1989 | Barder | 210/674 |

OTHER PUBLICATIONS

Russian Author's Certificate No. 681,043, published Aug. 25, 1979.

Primary Examiner—John Kight, III
Assistant Examiner—Dennis R. Daley
Attorney, Agent, or Firm—Thomas K. McBride; John F. Spears, Jr.; Jack H. Hall

[57] ABSTRACT

An adsorptive separation process for separating sterols from a feed mixture, especially one that is acid-free, containing sterols, e.g., tan oil, wool fat, etc., which process comprises contacting the feed mixture with an adsorbent comprising magnesium silicate (Florisil), selectively adsorbing substantially all of the sterols to be separated to the substantial exclusion of the other components and thereafter recovering high purity sterols. The adsorbed sterols are desorbed with methyl-t-butyl ether (MtBE), which is superior, as a desorbent, to previously used aromatic liquids, e.g., toluene and chlorobenzene. An especially suitable acid-free feed is produced from crude tall oil, without the need for pitching, by a liquid-liquid extraction with DMSO and hexane solvents added to the top and bottom of the extraction column, respectively, and feed introduced at an intermediate zone.

15 Claims, 2 Drawing Sheets

SEPARATION OF STEROLS FROM LOW-ACID FEEDS WITH MAGNESIUM SILICATE AND METHYL-TERT-BUTYL ETHER DESORBENT

BACKGROUND OF THE INVENTION

1. Field of the Invention

The field of art to which this invention pertains is the separation of sterols from crude tall oil, tall oil pitch or wool fat. Specifically, it relates to the concentration of sterols in the unsaponifiable fraction of crude tall oil and the separation of high purity sterols therefrom by a solid-bed adsorptive separation, which requires a low-acid sterol feed source. A liquid-liquid extraction process can provide a low-acid, sterol-containing feed directly from crude tall oil. The improved adsorption process utilizes magnesium silicate (Florisil) as adsorbent with a desorbent not previously used.

2. Background Information

It is known in the art to separate sterols from tall oil fractions, e.g., pitch, and from wool fat by adsorption and also by liquid-liquid extraction.

U.S. Pat. No. 4,664,807 discloses the method of isolating cholesterol from tall oil pitch, or other sterol containing materials, in an adsorption column packed with alumina, magnesium silicate (Florisil) or silica gel and eluting the cholesterol with a liquid such as heptane-acetone (19:1) (v:v), toluene-acetone (29:1) (v:v), toluene, heptane-n-butyl acetate (5:1) (v:v) or heptane-toluene-acetone (70:1:9) (v:v:v).

Also in Julian U.S. Pat. No. 3,840,570, sterols are obtained in purified form through a series of steps initiated by a solvent extraction of sterol esters from tall oil pitch utilizing an alcohol/hydrocarbon solvent mixture. In the solvent extraction step, the pitch is first dissolved in the solvent mixture and, after the addition of water, separates into an upper hydrocarbon layer which contains nearly acid-free sterol esters and a lower, alcohol-water phase which contain acids, which are then separated mechanically. Saponification of the hydrocarbon layer containing the sterol esters is followed by additional purification steps to recover the concentrated sterols.

Also, as disclosed in Russian Author's Certificate No. 681,043, published Aug. 25, 1979, tall oil and a polar solvent, e.g., dimethylsulfoxide (hereinafter DMSO), dimethylformamide, acetonitrile or dimethylpyrrolidine is fed into the top portion of an extraction column and a non-polar solvent, e.g., hexane is fed into the bottom portion. Unsaponifiable substances are recovered, after phase separation, in the non-polar solvent and fatty acids and resin acids are recovered in the polar solvent. One objective of the authors is to recover a fatty acid fraction in the polar phase (DMSO) having less than 3% unsaponifiables, but sterols are not mentioned nor is the effect of acid in the unsaponifiable fraction. No mention is made of the use of separate input streams for DMSO, crude tall oil feed and hexane with the feed introduced in an intermediate zone in order to obtain a substantial reduction in the acid in the hexane extract phase.

Tall oil contains several sterols, including campesterol, α- and β-sitosterol, the latter of which is especially used in cosmetics, such as moisturizing cream, lipstick, etc., as an emulsifier, viscosity regulator, emulsion stabilizer, and skin softener. Wool fat contains cholesterol, which has the same uses listed above. Sterols from both sources also have medicinal uses and are useful chemical intermediates.

Crystalline aluminosilicates or zeolites having high physical strength and attrition resistance, are used in adsorption separations of various mixtures in the form of agglomerates. Methods for forming the crystalline powders into such agglomerates include the addition of an inorganic binder, generally a clay, comprising silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type or silica are generally used. It is also known that water permeable organic polymers are superior binders.

The invention herein can be practiced in fixed or moving adsorbent bed systems by batch or continuous processes, but the preferred system for this separation is a continuous countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. No. 3,040,777 and 3,422,848. Flow rates in the various zones may be set and regulated by a programmed flow controller. Equipment utilizing these principles are familiar, in sizes ranging from pilot plant scale (deRossett U.S. Pat. No. 3,706,812) to commercial scale with flow rates from a few cc per hour to many thousands of gallons per hour.

The functions and properties of adsorbents and desorbents in the chromatographic separation of liquid components are well-known, but for reference thereto, Zinnen et al. U.S. Pat. No. 4,642,397 is incorporated herein.

It is an object of the present invention to separate sterols, as a class, from any available sterol-containing natural or synthetic materials, thereby obtaining said sterols in greater purity and increased recovery.

An object is to provide an adsorptive separation process for obtaining high purity sterols from various feed sources using a superior adsorbent which is capable of isolating substantially more of the sterols contained in the feed than with the disclosure of a continuous, simulated moving bed adsorption separation process in co-pending application Ser. No. 131,611, filed Dec. 11, 1987, wherein activated carbon is the adsorbent used; to avoid deactivation of the Florisil adsorbent, however, it is essential that the acid in the feed be no more than about 1%.

It is a further object to provide a dramatically improved desorbent for the chromatographic separation that gives a 250% increase in selectivity compared to prior art desorbents, e.g., toluene.

Another object of this invention is to produce a sterol fraction directly from crude tall oil by a combination of a liquid-liquid extraction process which provides a relatively acid-free sterol fraction and a chromatographic adsorptive process which is most advantageous when a low acid feed is used.

It is a further object to obtain very pure sterols in good yield from tall oil sources without first having to pitch the crude tall oil, a process that includes heating the crude tall oil to high temperatures under vacuum. The pitching treatment reduces the recovery of sterols possible because some of the sterols are dehydrated under those conditions.

SUMMARY OF THE INVENTION

The invention comprises a process for separating sterols from the acid components of crude tall oil, without pitching the crude tall oil, by a chromatographic process in which magnesium silicate is the adsorbent. We have found that methyl-t-butyl ether (sometimes hereinafter MtBE) is a superior desorbent for recovering sterols separated from tall oil or wool fat feeds by a magnesium silicate sieve, e.g., Florisil.

It is essential to a continuous commercial process in which the adsorbent is Florisil; that the feed be relatively acid-free. Therefore, acids present in the feed should be substantially removed or reduced to at least 1% prior to the adsorption separation process herein disclosed. This can be accomplished by known techniques, such as neutralization or esterification followed by water extraction. We have found that it is also possible to concentrate the sterols and reduce the acid concentration to quite low levels by liquid-liquid extraction with DMSO and hexane, before neutralization, as described herein.

By this invention, and particularly a two-stage process involving the aforementioned liquid-liquid extraction followed by an adsorptive separation, sterols can be separated from sterol-containing feeds in very high purity exceeding 80% and up to about 95% and with the recovery of a high proportion of the sterols in the feed of from 50 to 95%.

The invention, in one aspect, is a continuous process for separating sterols from an acid-free tall oil or wool fat feed mixture comprising said sterols, which process comprises (i.) contacting at adsorption conditions the mixture with an adsorbent comprising a magnesium silicate molecular sieve while (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed inlet stream at an upstream boundary of the zone and a raffinate outlet stream at a downstream boundary of the zone; (c) maintaining a purification zone immediately upstream from the adsorption zone, the purification zone defined by the adsorbent located between an extract outlet stream at an upstream boundary of the purification zone and the feed inlet stream at a downstream boundary of the purification zone and (d) maintaining a desorption zone immediately upstream from the purification zone, the desorption zone defined by the adsorbent located between a desorbent inlet stream at an upstream boundary of the zone and the extract outlet stream at a downstream boundary of the zone; (ii.) passing the feed stream into the adsorption zone at adsorption conditions to effect the selective adsorption of the sterols by the adsorbent in the adsorption zone and withdrawing a raffinate outlet stream from the adsorption zone; (iii.) contacting the adsorbent with a desorbent material in said desorption zone at desorption conditions to effect the displacement of the adsorbed sterols from the adsorbent; (iv.) withdrawing an extract stream comprising sterols and desorbent material from the desorption zone; (v.) periodically advancing through the column of adsorbent in a downstream direction with respect to fluid flow in the adsorption zone, the feed inlet stream, raffinate outlet stream, desorbent inlet stream, and extract outlet stream to effect the shifting of zones through the adsorbent and the production of extract outlet and raffinate outlet streams, the improvement wherein the desorbent comprises methyl-t-butyl ether.

In a further aspect, the invention comprises a process for concentrating the sterols and substantially lowering the concentration of acids in a feed mixture comprising said sterols and other neutral materials, fatty acids and rosin acid, said process comprising: (a) introducing said feed mixture into an extraction zone at an intermediate location thereof, and therein contacting said mixture with a polar and a non-polar solvent, said polar solvent comprising dimethylsulfoxide (DMSO) and said non-polar solvent comprising hexane; (b) introducing said DMSO into said extraction zone at one end thereof; (c) introducing said hexane into said extraction zone at the other end thereof; (d) removing a sterol-rich hexane extract stream from said extraction zone which contains a higher concentration of said sterols, on a solvent-free basis, than said feed mixture and a substantially lower concentration of acids; (e) removing an acid-rich DMSO extract stream from said extraction zone containing a higher concentration of said fatty or rosin acid, on a solvent free basis, than said feed mixture.

Another aspect of the invention is a two-stage process, combining the above process steps, wherein the feed to the adsorptive separation is pretreated by a liquid-liquid extraction process to remove acids therefrom and concentrate the sterol fraction. The liquid-liquid extraction process employs DMSO and hexane as dual extractive solvents, the improvement comprising introducing the feed to an intermediate zone in the extraction column. The unsaponifiable components of the crude tall oil can be removed from the sterols by the adsorptive separation of this invention with Florisil as adsorbent and MtBE as desorbent.

In a preferred embodiment, acid concentrations in the sterol fraction lower than 1% are achieved by a liquid-liquid fractional extraction comprising the steps of: (1) introducing said feed mixture into an intermediate zone of an extraction column, and therein contacting of said mixture with a polar and a non-polar solvent, said polar solvent comprising dimethylsulfoxide (DMSO) and said non-polar solvent comprising hexane; (2) introducing said DMSO at high flow rates into said extraction column at one end thereof; (3) introducing said hexane at low flow rates into said extraction column at the other end thereof; (4) removing a sterol-rich hexane extract stream from said extraction column which contains a higher concentration of said sterols, on a solvent-free basis, said feed mixture and a substantially lower concentration of acids; and (5) removing an acid-rich DMSO extract stream from said extraction column containing a higher concentration of said fatty or rosin acids, on a solvent free basis, than said feed mixture.

Other objectives and embodiments of the invention encompass details about feed mixtures, adsorbents, desorbent materials, solvents, and operating conditions, all of which are hereinafter disclosed in the following discussion of each of the facets of the present invention.

DETAILED DESCRIPTION OF THE INVENTION

The adsorbent of this invention is magnesium silicate, available as Florisil, which has a high capacity for adsorbed materials.

Feed mixtures that can be used in the process of this invention include crude tall oil or tall oil pitch, which contains primarily $\beta$-sitosterol, from which the acidic materials have been removed or neutralized. Other sources of sterols, including wool fats, from which cholesterol can be obtained, are useful feed materials for separation by this invention. Acidic materials in the feed, however, will deactivate the Florisil so rapidly that the separation by a continuous process would be of little commercial value. However, Florisil, as adsorbent, is quite effective in producing a highly purified sterol extract component and, therefore, obtaining sterols commercially in a continuous process, such as Sorbex, e.g., the process disclosed in Broughton, supra, from acid-free feeds, is possible using a novel desorbent. To separate the sterols from a low-acid feed mixture containing a mixture of sterols, the feed mixture is contacted with the magnesium silicate adsorbent. The sterols are more selectively adsorbed and retained by the adsorbent while the other feed constituents are relatively unadsorbed and are removed from the interstitial void spaces between the particles of adsorbent and from the surface of the adsorbent.

An adsorption column is used to separate the sterols in the feed by selectively adsorbing said sterols onto an adsorbent and thereafter desorbing the adsorbed components of the feed with a desorbent in the manner described in the aforementioned Broughton U.S. Pat. No. 2,985,589 and others mentioned above.

Sterol products having high purity at high recoveries, are recovered by desorbing the adsorbed sterols with methyl-t-butyl ether (MtBE). MtBE satisfies well-known criteria for desorbents, i.e., it displaces the adsorbed sterol from the adsorbent with reasonable mass flow rates without itself being so strongly adsorbed as to unduly prevent the sterol from displacing the desorbent material in a following adsorption cycle, it is compatible with the particular adsorbent and the particular feed mixture and it does not reduce or destroy the critical selectivity of the adsorbent for the sterol with respect to the desorbent.

Moreover, MtBE exhibits a selectivity relationship with respect to each of the fractions of the feed for the particular adsorbent that enhances the separation process. Specifically, the selectivity for adsorption of the extract (sterols) fraction with respect to the desorbent, (MtBE), is slightly greater than 1 while the selectivity of the raffinate components, (non-sterols), combined or separately, with respect to the desorbent, MtBE is a fraction, i.e., less than 1. This balance of selectivities makes it possible for the desorbent to replace the extract as the adsorbed material while preventing the raffinate materials from displacing the desorbent. The adsorbent can be contained in one or more chambers where, through programmed flow into and out of the chambers, separation of the sterols is effected. The adsorbent will preferably be contacted with a desorbent material which is capable of displacing the adsorbed sterols from the adsorbent. The resultant extract stream comprising the sterols and desorbent material may be subjected to a separation step, e.g., fractionation, so as to obtain high purity sterols. The desorbent can be recycled to the adsorption column and added to makeup desorbent.

The adsorbent may be employed in the form of a dense compact fixed bed which is alternately contacted with the feed mixture and desorbent materials. The adsorbent may be in the form of one or more static beds with appropriate valving, but countercurrent moving-bed or simulated moving-bed countercurrent flow systems have a much greater separation efficiency than fixed adsorbed bed systems and are, therefore, preferred for use in our separation process.

Adsorption and desorption conditions for adsorptive separation processes can generally be either in the liquid or vapor phase or both. Preferred adsorption conditions for the process of this invention will include temperatures within the range of from about 20° to about 230° C. and will include pressures sufficient to maintain liquid phase, which will be in the range from about atmospheric to about 500 psig, preferably from 100 to about 350 psig. Pressures higher than about 500 psig do not appear to affect the selectivity to a measurable amount and additionally would increase the cost of the process. Desorption conditions for the process of the invention shall generally include the same range of temperatures and pressures as described for adsorption operations.

Feed Preparation.

As previously stated, the adsorption separation process of this invention requires that the acid be removed from the sterol-containing feed so that the adsorbent will have a commercially-acceptable life. Otherwise, acids in the feed will quickly deactivate the Florisil adsorbent, and require too frequent regeneration. Conventional techniques are available for the removal of acid from the sterol-containing feed material, e.g., neutralization or esterification with bases, and hydroxides, hydroxy group-containing organic compounds, amines, etc. The reaction product can be extracted from organic components by water.

Another technique for preparing an acid-free feed to the Florisil/MtBE adsorption separation process involves another adsorptive separation process, such as described in copending application Ser. No. 131,611, filed Dec. 11, 1987, and incorporated by reference herein. In that preparation, activated carbon, e.g., OL Carbon from Calgon Corp. was used as the adsorbent to remove sterols from tall oil. The sterols are adsorbed to the substantial exclusion of fatty and rosin acids and can be recovered by desorption with chlorobenzene to provide a substantially acid-free sterol feed. The feeds described in the application are tall oil pitches, but crude tall oil may also be used in this invention.

A novel technique which is an improvement over the Russian Authors' Certificate previously mentioned, for preparing crude tall oil as feed for the adsorption separation, is disclosed hereinafter. Sterol products having a higher purity and yield of sterols can be obtained at a lower cost than was previously possible. This is achieved partially through the elimination of the pitching step, which adds to the cost of the product and lowers the amount of sterols available for recovery, as aforementioned, but also through the use of Florisil in the adsorption separation, which gives better yield and recovery than other known adsorbents. The ability of the Florisil to recover sterols economically is dependent upon having a low acid sterol-containing feed available. The main feature of the liquid-liquid extraction process is the use of three input streams, with the feed stream being introduced in a zone intermediate the upper and lower points where the DMSO and hexane are added as shown in the flow diagram of FIG. 1. In the optimum case, DMSO is fed at a low rate with feed at an intermediate point, e.g., the tenth plate in a twenty plate (theoretical) column, at a high rate to the top of the column and hexane is fed at a low rate to the bottom. Specifically, it is calculated that the overhead will be substantially acid-free at the following rates (based on total solvent throughput):
DMSO (to top): 75% (Vol.)
DMSO (to middle): 12% (Vol.)
hexane (to bottom): 13% (Vol.)
Acceptable acid content (less than 1%) can be achieved with solvent rates (same basis as above) in the following ranges:
DMSO (to top): 53 to 81% (Vol.)
DMSO (to middle): 6 to 36% (Vol.)
hexanine (to bottom): 11 to 15% (Vol.)
Greater amounts of acid in the hexane phase overhead, which would contain higher concentrations of sterols than the feed, could be reduced sufficiently before subjecting the overhead to the adsorptive separation by either treating the overhead with aqueous NaOH to neutralize and extract the acid components or treating with excess methanol to form esters which can remain in the feed since the latter are not deleterious to the Florisil adsorbent. An intermediate adsorptive separation can also be used to advantage, in certain cases, after removal of the solvent from the hexane phase, to further concentrate the sterols before the adsorptive separation with Florisil is conducted. The separation uses a nonactivated type carbon adsorbent and conditions disclosed in copending application, Ser. No. 131,612, which is hereby incorporated by reference.

Liquid-liquid extraction devices are well known to the art. Furthermore, fractional liquid-liquid extraction devices, which employ dual mutually immiscible solvents are known, and the improved process effectively utilizes this class of extraction devices. Generally, the primary component of the device will comprise a vertical column containing internals such as perforated plates or packing, which ensure intimate contact of the two phases. The heavier phase, such as the DMSO solvent phase of the present invention, is introduced at the top of the column, while the lighter phase, such as the hexane solvent phase of the present invention, is introduced at the bottom. The crude tall oil feed is introduced into an intermediate zone near the middle of the column. The immiscible liquid phases pass each other in countercurrent flow and intimate admixture throughout the column whereby each of the phases becomes enriched in certain components of the feed material, e.g., the sterols are selectively recovered in the hexane phase in which they have a greater solubility. The DMSO phase leaving the bottom of the column is referred to as the extract stream, and the hexane phase leaving the top of the column is referred to as the raffinate stream. DMSO and hexane may be recovered from the extract and raffinate streams, respectively, for reuse in the system by conventional means such as distillation, before feeding the extract stream to the adsorptive separation.

In the two-stage, or combined, process referred to above, the liquid-liquid extraction process disclosed above can be employed to produce the acid-free feed to the adsorptive separation process for obtaining a final, high-purity sterol product. Referring to the flow diagram in FIG. 1, crude tall oil is fed to an intermediate plate of a liquid-liquid extraction column with DMSO, DMSO is fed to the top of the column and hexane is fed to the bottom. The DMSO fraction is removed from the bottom of the column and contains substantially all of the fatty acids and rosin acids present in the original feed. The hexane fraction, which is greatly concentrated in sterols and contains other neutrals, as well, is removed in the overhead (raffinate) and fed to the adsorption column after distilling to remove the hexane. Likewise, the extract can be fractionated to separate the DMSO from the acid fraction to be recycled to the extraction column.

Figure 1:
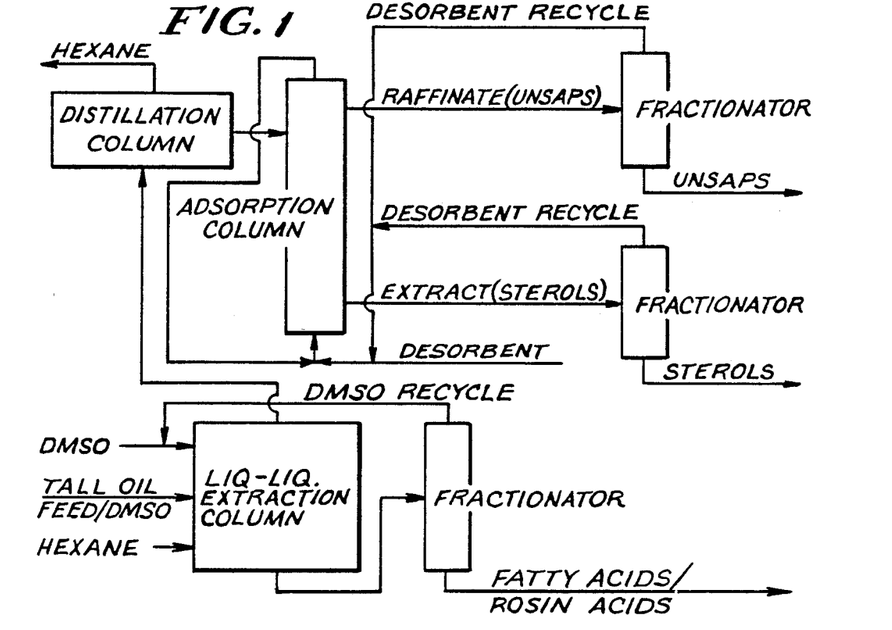
FIG. 1 is a flow diagram of the 2-stage combined process showing an adsorption column and a liquid-liquid extraction column having upper and lower points for introducing DMSO and hexane, respectively and an intermediate point at which the feed is introduced to the extraction column.

In the adsorption column, loaded with Florisil, the sterols are selectively adsorbed and thus can be separated from the other neutrals remaining in the feed by desorbing with MtBE. The sterols in the extract stream from the adsorption column can be fractionated conventionally to remove the desorbent, which is recycled to the adsorbent column. The raffinate stream contains neutral materials (unsaponifiables), which are not adsorbed by the Florisil adsorbent, and desorbent. The desorbent in the raffinate can also be recovered for recycling by a conventional fractionating step.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipement is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed, diluted with desorbent, is injected for a duration of several minutes. Desorbent flow is resumed, and the tracer and the feed components are eluted as in a liquid-solid chromatographic operation. The effluent is collected in fractions and analyzed using chromatographic equipment and traces of the envelopes of corresponding component peaks are developed.

From information derived from the test, adsorbent performance can be rated in terms of retention volume for an extract or a raffinate component, selectivity for one component with respect to the other, and the rate of desorption of an extract component by the desorbent.

The net retention volume (NRV) of an extract or a raffinate component may be characterized by the distance between the center of the peak envelope of the extract or raffinate component and the peak envelope of the tracer component or some other known reference point. It is expressed in terms of the volume in cubic centimeters of desorbent pumped during this time interval represented by the distance between the peak envelope centers.

Selectivity, ($\beta$), with regard to two given components, is equal to the quotient obtained by dividing the respective net retention volumes of such components. Where selectivity of two components approaches 1.0 there is no preferential adsorption of one component by the adsorbent with respect to the other; they are both adsorbed (or non-adsorbed) to about the same degree with respect to each other. As the ($\beta$) becomes less than or greater than 1.0, there is a preferential adsorption by the adsorbent for one component with respect to the other. When comparing the selectivity by the adsorbent of one component C over component D, a ($\beta$) larger than 1.0 indicates preferential adsorption of component C. A ($\beta$) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. Selectivity ($\beta_i$), of one of the components relative to the desorbent is obtained in the same manner, using the NRV of the desorbent as determined by the adsorptive capacity of Florisil (16% of adsorbent volume).

Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While toluene, which has been previously used as a single element in separating sterols in adsorption processes using Florisil, does not destroy the selectivity of the adsorbent for the feed mixture, toluene is less strongly adsorbed than all the components of tall oil, namely, sterols, lights and heavies (see Table 3). The latter situation, in which the desorbent selectivities are not balanced for extraction of the sterols and rejection of the other components involved, leads to an inefficient performance of a continuous countercurrent adsorptive process such as that described in the Broughton Patent above. As will also be seen from Table 3 in Example I, MtBE is more strongly adsorbed than either of the raffinate components, but less strongly adsorbed than the sterol extract component.

EXAMPLE I

Figure 2:
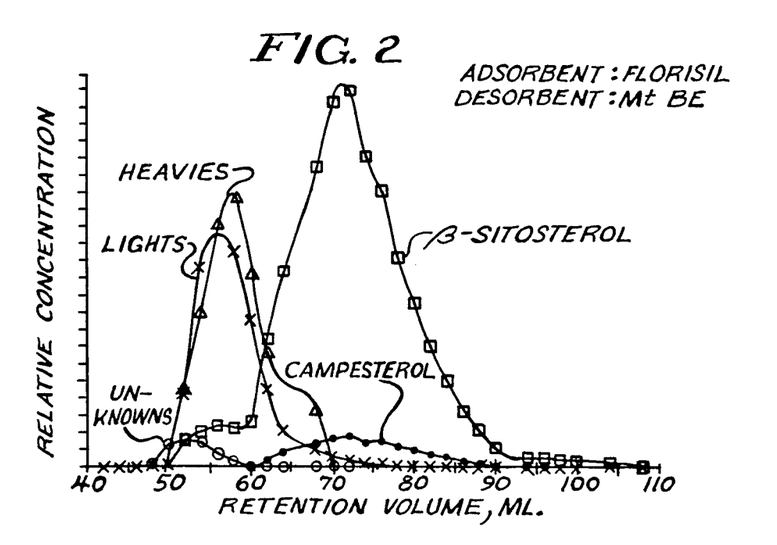
FIG. 2 is a trace of the chromatographic separation of Example I, employing Florisil adsorbent and MtBE desorbent.

A pulse test was conducted on the above described pulse test apparatus. The adsorbent column was helical with capillary controlled pressure, sufficient to maintain liquid phase. A feed pulse of 5 ml, 20% by wt. of a processed tall oil pitch containing about 37% (wt.) total sterols, primarily $\beta$-sitosterol, and having an ASTM acid number of 2.0 was flowed transversely through the column at a rate of 1.3 ml/min. The adsorbent chamber was packed with magnesium silicate (Florisil—available from Floridin Company) having particle sizes from 20 to 50 mesh. Following the feed pulse, methyl-t-butyl ether desorbent flow was resumed. The results of the pulse test are shown in FIG. 2 and the following Table 1. Net retention volume (NRV) is calculated as the difference between the gross retention volume (GRV) of the component and the void volume (or the GRV of a non-adsorbed paraffin tracer).

TABLE 1

| Component | GRV(cc)* | NRV (cc) | $\beta$ |
| --- | --- | --- | --- |
| Lights | 56.8 | 8.3 | 2.76 |
| Unknowns | 52.5 | 4.0 | 5.75 |
| Campesterol | 72.5 | 24.0 | 0.95 |
| $\beta$-Sitosterol | 71.4 | 22.9 | Ref. |
| Heavies | 57.5 | 9.0 | 2.55 |

*Void volume = 48.5 cc.

Figure 3:
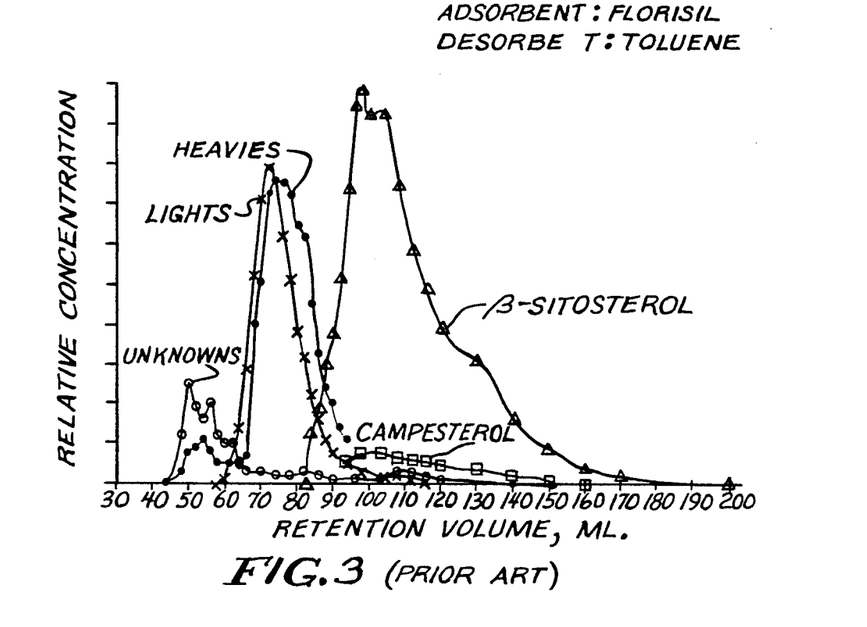
FIG. 3 is a trace of the chromatographic separation of Example I, employing the prior art desorbent toluene.

Sterols were also separated from another sample of the same tall oil pitch following the procedure just described, except that toluene was used as the desorbent. The pulse test results and the selectivities ($\beta$) are shown in FIG. 3 and listed in the following Table 2.

TABLE 2

| Component | GRV (cc)* | NRV (cc) | $\beta$ |
| --- | --- | --- | --- |
| Lights | 73.3 | 24.8 | 2.22 |
| Unknowns | 81.3 | 32.8 | 1.69 |
| Campesterol | 111.3 | 62.8 | 0.88 |
| $\beta$-Sitosterol | 103.7 | 55.2 | Ref. |
| Heavies | 76.5 | 28.0 | 1.97 |

*Void volume = 48.5 cc.

Calculations of the desorbent selectivities ($\beta_i$) of the various fractions of the feed relative to each desorbent used above were made as previously described and the results are set forth in Table 3.

TABLE 3

| Fraction | $\beta_i$ (MtBE) | $\beta_i$ (Toluene) |
| --- | --- | --- |
| Lights | 0.68 | 2.04 |
| Unknowns | 0.33 | 2.70 |
| Campesterol | 1.97 | 5.16 |
| $\beta$-Sitosterol | 1.88 | 4.54 |
| Heavies | 0.74 | 2.30 |

An analysis of the above results will clearly demonstrate the benefits of methyl-t-butyl ether over the prior art desorbent, toluene. Desorbent, MtBE, is more strongly adsorbed than either lights or heavies, both of which are rejected by the adsorbent, and not as strongly adsorbed as the extract fraction, primarily the sterols. Toluene, on the other hand, is less strongly adsorbed than each of the fractions, i.e., both the rejected fraction, or raffinate, and the adsorbed fraction, or extract. In a continuous process, such as the countercurrent simulated moving bed process described in Broughton, supra, it is highly advantageous, resulting in greater efficiency, that the desorbent selectivity with respect to the fractions be "balanced" in the above manner as described for MtBE. Because toluene is less strongly adsorbed than both the raffinate and extract materials, it results in a very inefficient performance in the separation of sterols from tall oil in a continuous countercurrent simulated fixed bed operation.

EXAMPLE II

A tall oil pitch was treated by the adsorbent, OL Carbon from Calgon Corp. to concentrate the sterols in the extract, which was desorbed with chlorobenzene, as described in Example II copending application Ser. No. 131,611. A sample extract from that run was taken and had the following composition:

| Component | Wt. % |
|---|---|
| Campesterol | 8.5 |
| Campestanol | 1.1 |
| β-Sitosterol | 51.2 |
| β-Sitostanol | 10.6 |
| α-Sitosterol | 3.1 |
| Unknown sterols | 4.6 |
| Unknowns | (Bal.) |
| Total | 100 |

Figure 4:
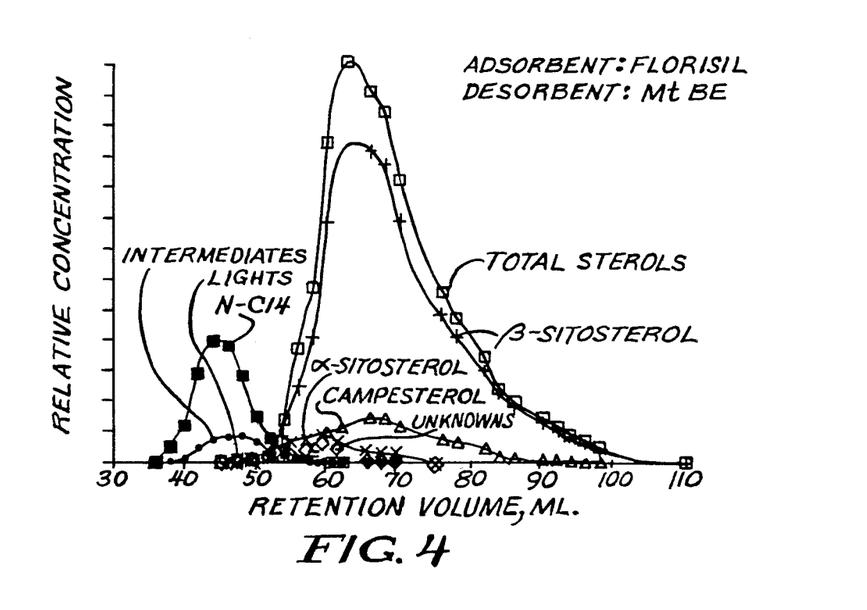
FIG. 4 is a trace of the chromatographic separation of Example II, also employing the Florisil/MtBE adsorbent-desorbent combination.

The extract, substantially acid-free, was fed to the pulse test apparatus, described above, containing Florisil adsorbent and the sterols were preferentially adsorbed onto the Florisil and desorbed with 100% MtBE at 134° C. The results of the separation are shown in FIG. 4 and the following Table 4.

| Components | GRV | NRV | β |
|---|---|---|---|
| n-C$_{14}$ | 45.1 | 0.0 | tracer |
| Lights | 55.8 | 10.7 | 2.06 |
| Intermediates | 47.2 | 2.1 | 10.49 |
| Total Sterols | 66.7 | 21.6 | 1.02 |
| Campesterol | 67.4 | 22.4 | 0.98 |
| β-Sitosterol | 67.0 | 21.9 | Reference |
| α-Sitosterol | 59.7 | 14.7 | 1.50 |
| Unknown | 59.6 | 14.5 | 1.51 |

The intermediates include dehydrated sterols and rosin materials. It is possible to obtain sterols having greater than 95% purity with the acid-free feed of this example.

EXAMPLE III

Feed Preparation.

An acid-free, concentrated sterol fraction suitable for the adsorptive separation of Examples I and II can be obtained from crude tall oil feed in a liquid-liquid fractional extraction column, substantially as previously described, in which the non-polar solvent is hexane and the polar solvent is DMSO. DMSO solvent is fed at the top of the extraction column of FIG. 1 and n-hexane non-polar solvent is fed to the bottom of the column. A DMSO fraction containing fatty acids and rosin acids can be obtained and DMSO can be recovered by fractionation and recycled to the process. Hexane may also be recovered by fractionation before sending the concentrated sterol fraction to the adsorption separation column. The composition of the feed for the calculations below was assumed to be:

TABLE 5

| Component | Feed (wt. %) |
|---|---|
| Rosins | 35 |
| Saturated fatty acids | 5 |
| mono-unsaturated fatty acids | 20 |
| di-unsaturated fatty acids | 15 |
| light neutrals | 17 |
| heavy neutrals | 8 |
| | 100 |

Calculations, based on a liquid-liquid extraction model based on DMSO-hexane, assuming 20 theoretical plates with feed to the 10th plate, were made to predict the optimum conditions for recovering a substantially acid-free sterol fraction from crude tall oil. The following Table 5 gives several sets of conditions possible for recovering at least 60% of the sterols in the feed with less than 1% acid content. Neutrals in the raffinate fraction include the sterols. All solvent flow rates are on a volume basis unless stated otherwise.

TABLE 6

| | Fraction of Total Solvent | | | Fraction of Raffinate Composition | | Sterols Recovered as Fraction of Sterols in Feed |
|---|---|---|---|---|---|---|
| Run No. | DMSO to top | DMSO with feed | Hexane to Bottom | Fatty Acids | Neutrals | |
| 1 | 0.53 | 0.36 | 0.11 | 0.01 | 0.99 | 0.61 |
| 2 | 0.70 | 0.18 | 0.12 | 0.00 | 1.00 | 0.60 |
| 3 | 0.65 | 0.23 | 0.12 | 0.01 | 0.99 | 0.66 |
| 4 | 0.59 | 0.29 | 0.12 | 0.01 | 0.99 | 0.71 |
| 5 | 0.81 | 0.06 | 0.13 | 0.00 | 1.00 | 0.66 |
| 6 | 0.75 | 0.12 | 0.13 | 0.00 | 1.00 | 0.72 |
| 7 | 0.70 | 0.17 | 0.13 | 0.01 | 0.99 | 0.76 |
| 8 | 0.64 | 0.23 | 0.13 | 0.01 | 0.99 | 0.80 |
| 9 | 0.80 | 0.06 | 0.14 | 0.01 | 0.99 | 0.82 |
| 10 | 0.75 | 0.11 | 0.14 | 0.01 | 0.99 | 0.85 |
| 11 | 0.79 | 0.06 | 0.15 | 0.01 | 0.99 | 0.91 |

In general, the preferred conditions for the liquid-liquid extraction are: low DMSO throughput with the feed; high DMSO rate to the top of the column and low hexane rate to the bottom of the column. The optimum conditions for this column appears to be Run No. 6 where the DMSO (top):DMSO (feed):hexane rates are 75:12:13. Other rates within the scope of the preferred embodiment for obtaining a substantially acid-free feed for the Florisil/MtBE adsorptive separation will be apparent from the table and fall within the ranges: DMSO (top) 0.53 to 0.81; DMSO (feed) 0.06 to 0.36 and hexane 0.11 to 0.15, respectively. Other columns with different numbers of theoretical plates may be used with varying results as will be understood by persons skilled in the art of liquid extraction.

What is claimed is:

1. A process for separating sterols in high purity from a feed mixture containing said sterols which process comprises contacting at adsorption conditions said mixture with an adsorbent comprising a magnesium silicate molecular sieve, selectively adsorbing said sterols to the substantial exclusion of other components of said feed, and contacting the adsorbent containing said sterols with a desorbent material comprising methyl-t-butyl ether to desorb said sterols therefrom as a fluid extract stream.

2. The process of claim 1 further characterized in that said feed mixture is substantially acid-free crude tall oil.

3. The process of claim 1 wherein said feed mixture is treated to substantially reduce the amount of acids in said feed mixture.

4. The process of claim 1 further characterized in that said adsorption conditions include a temperature within the range of from about 20° to about 230° C. and at a pressure within the range of from about atmospheric to about 500 psig.

5. The process of claim 2 wherein said sterols comprise primary β-sitosterol.

6. The process of claim 3 wherein said treatment comprises liquid-liquid extraction, the steps comprising:
  (1) introducing said feed mixture into an intermediate zone of an extraction column, and therein contacting said mixture with a polar and a non-polar solvent, said polar solvent comprising dimethylsulfoxide (DMSO) and said non-polar solvent comprising hexane;

(2) introducing said DMSO into said extraction column at one end thereof;

(3) introducing said hexane into said extraction column at the other end thereof;

(4) removing a sterol-rich hexane extract stream from said extraction column which contains a higher concentration of said sterols, on a solvent-free basis, said feed mixture and a substantially lower concentration of acids; and (5) removing an acid-rich DMSO extract stream from said extraction column containing a higher concentration of said fatty or rosin acid, on a solvent free basis, than said feed mixture.

7. The process of claim 6 wherein said feed mixture comprises crude tall oil.

8. In a process for separating sterols in high purity from a feed mixture containing said sterols which comprises:

(i.) contacting said mixture at adsorption conditions with an adsorbent comprising a magnesium silicate molecular sieve while (a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed inlet stream at an upstream boundary of said zone and a raffinate outlet stream at a downstream boundary of said zone;

(c) maintaining a purification zone immediately upstream from said adsorption zone, said purification zone defined by the adsorbent located between an extract outlet stream at an upstream boundary of said purification zone and said feed inlet stream at a downstream boundary of said purification zone; and (d) maintaining a desorption zone immediately upstream from said purification zone, said desorption zone defined by the adsorbent located between a desorbent inlet stream at an upstream boundary of said zone and said extract outlet stream at a downstream boundary of said zone;

(ii.) passing said feed stream into said adsorption zone at adsorption conditions to effect the selective adsorption of said sterols by said adsorbent in said adsorption zone and withdrawing a raffinate outlet stream from said adsorption zone;

(iii.) contacting said adsorbent with a desorbent material in said desorption zone at desorption conditions to effect the displacement of said sterols from the adsorbent;

(iv.) withdrawing an extract stream comprising said sterols and desorbent material from said desorption zone; and (v.) periodically advancing through said column of adsorbent in a downstream direction with respect to fluid flow in said adsorption zone, the feed inlet stream, raffinate outlet stream, desorbent inlet stream, and extract outlet stream to effect the shifting of zones through said adsorbent and the production of extract outlet and raffinate outlet streams, the improvement comprising using methyl-t-butyl ether as said desorbent.

9. The process of claim 8 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

10. The process of claim 8 further characterized in that said adsorption conditions and desorption conditions include a temperature within the range of from about 20° to about 230° C. and a pressure within the range of from about atmospheric to about 500 psig.

11. The process of claim 8 wherein said feed is a crude tall oil.

12. The process of claim 11 wherein prior to step (i), said feed mixture is treated to remove substantial amounts of acid from said feed mixture.

13. The process of claim 12 wherein said treatment comprises:

(1) introducing said feed mixture into an intermediate zone of said extraction column, and therein contacting said mixture with a polar and a non-polar solvent said polar solvent comprising dimethylsulfoxide (DMSO) and said non-polar solvent comprising hexane;

(2) introducing said DMSO into said extraction column at one end thereof;

(3) introducing said hexane into said extraction column at the other end thereof;

(4) removing a sterol-rich hexane extract stream from said extraction column which contains a higher concentration of said sterols, on a solvent-free basis, said feed mixture and a substantially lower concentration of acids;

(5) removing an acid-rich DMSO extract stream from said extraction column containing a higher concentration of said fatty or rosin acid, on a solvent free basis, than said feed mixture.

14. A process for concentrating sterols in a feed mixture comprising said sterols, fatty acids and rosin acid, said process comprising:

(a) introducing said feed mixture into an extraction zone at an intermediate location thereof, and therein contacting said mixture with a polar and non-polar solvent, said polar solvent comprising dimethylsulfoxide (DMSO) and said non-polar solvent comprising hexane;

(b) introducing said DMSO into said extraction zone at one end thereof;

(c) introducing said hexane into said extraction zone at the other end thereof;

(d) removing a sterol-rich hexane extract stream from said extraction zone which contains a higher concentration of said sterols, on a solvent-free basis, than said feed mixture and a substantially lower concentration of acids; and (e) removing an acid-rich DMSO extract stream from said extraction zone containing a higher concentration of said fatty or rosin acid, on a solvent free basis, than said feed mixture.

15. The process of claim 14 wherein the solvent rates are in the following ranges: DMSO to the top of said extraction zone is 53 to 81% (based on total solvent throughput); DMSO with said feed is 6 to 36% and hexane to the bottom of said extraction zone is 11 to 15%.

* * * * *

UNITED STATES PATENT AND TRADEMARK OFFICE
CERTIFICATE OF CORRECTION

PATENT NO. : 4,977,243
DATED : December 11, 1990
INVENTOR(S) : Timothy J. Barder et al.

It is certified that error appears in the above-identified patent and that said Letters Patent is hereby corrected as shown below:

In Column 12, line 44: Delete "a";

line 45: Delete "molecular sieve";

line 62: Change "primary" to -- primarily --;

In Column 13, line 22: Delete "a";

line 23: Delete "molecular sieve".

Signed and Sealed this

Twenty-ninth Day of September, 1992

Attest:

DOUGLAS B. COMER

Attesting Officer

Acting Commissioner of Patents and Trademarks